(12) United States Patent
Qiao et al.

(10) Patent No.: US 8,129,144 B2
(45) Date of Patent: *Mar. 6, 2012

(54) PAPILLOMA PSEUDOVIRUS AND PREPARATION

(75) Inventors: Liang Qiao, Maywood, IL (US); Wei Shi, Maywood, IL (US); Yujun Huang, Maywood, IL (US); Jianzhong Liu, Maywood, IL (US)

(73) Assignee: Loyola University Chicago, Maywood, IL (US)

( * ) Notice: Subject to any disclaimer, the term of this patent is extended or adjusted under 35 U.S.C. 154(b) by 971 days.

This patent is subject to a terminal disclaimer.

(21) Appl. No.: 11/784,626

(22) Filed: Apr. 9, 2007

(65) Prior Publication Data

US 2010/0255027 A1    Oct. 7, 2010

Related U.S. Application Data

(63) Continuation of application No. 11/060,034, filed on Feb. 17, 2005, now Pat. No. 7,205,126, which is a continuation of application No. 10/294,087, filed on Nov. 14, 2002, now Pat. No. 6,878,541, which is a continuation of application No. PCT/CN02/00187, filed on Mar. 22, 2002.

(30) Foreign Application Priority Data

May 15, 2001   (CN) .................................. 01 1 18003

(51) Int. Cl.
   *C12P 21/06*   (2006.01)

(52) U.S. Cl. .................................... 435/69.1; 435/320.1

(58) Field of Classification Search ........................ None
See application file for complete search history.

(56) References Cited

U.S. PATENT DOCUMENTS 6,878,541 B2 *  4/2005  Qiao et al. ................. 435/320.1
7,205,126 B2 *  4/2007  Qiao et al. ................... 435/69.1

FOREIGN PATENT DOCUMENTS

| CN | 1241636 A | 1/2000 |
| CN | 1333338 A | 1/2002 |
| DE | 19526752 A | 1/1997 |
| JP | 2007-211026 | 8/2007 |
| WO | WO 99/50424 A | 10/1999 |
| WO | WO 01/71017 A2 | 9/2001 |
| WO | WO 02/092796 A1 | 11/2002 |

OTHER PUBLICATIONS

PCT Application No. PCT/CN2002/00187, International Search Report dated Aug. 22, 2002.
PCT Application No. PCT/CN2002/00187, International Preliminary Examination Report dated Sep. 23, 2002.
U.S. Appl. No. 10/294,087, Office Action dated Jan. 22, 2004.
U.S. Appl. No. 10/294,087, Office Action dated Jun. 23, 2004.
U.S. Appl. No. 10/294,087, Notice of Allowance dated Dec. 22, 2004.
U.S. Appl. No. 11/060,034, Office Action dated Feb. 10, 2006.
U.S. Appl. No. 11/060,034, Notice of Allowance dated Oct. 11, 2006.

* cited by examiner

*Primary Examiner* — Ali R. Salimi
(74) *Attorney, Agent, or Firm* — Henneman & Associates, PLC; Larry E. Henneman, Jr.

(57) ABSTRACT

The invention involves a papilloma pseudovirus that can induce immune response after oral intake as well as its preparation. It is characterized in that HPV or BPV pseudovirus are made by disrupting HPV-VLP or BPV-VLP, mixing them with plasmids (plasmids or DNA vaccine), and reassembling them into the pseudoviruses (VLPs with plasmids inside). Oral administration of the pseudoviruses will result in delivery to mucosal and systemic lymphoid tissues and induce immune responses for disease prevention and treatment. The pseudovirus induces stronger immune response than DNA vaccines. Additionally, the pseudovirus can be applied in gene therapy by bringing the therapeutic genes into lymphoid tissues in the human body.

20 Claims, 1 Drawing Sheet

PAPILLOMA PSEUDOVIRUS AND PREPARATION

RELATED APPLICATIONS

This application is a continuation of co-pending U.S. patent application Ser. No. 11/060,034, filed Feb. 17, 2005 by at least one common inventor, now U.S. Pat. No. 7,205,126, which is a continuation of U.S. patent application Ser. No. 10/294,087, filed on Nov. 14, 2002 by at least one common inventor and now issused as U.S. Pat. No. 6,878,541, which is a continuation of PCT/CN02/00187 filed on Mar. 22, 2002 by at least one common inventor, which claims priority to Application No. 01118003.X filed in China on May 15, 2001 (not published in English) by at least one common inventor, all of the foregoing applications and patents being incorporated herein by reference in their entireties.

GOVERNMENT LICENSE RIGHTS

The U.S. Government has a paid-up license in this invention and the right in limited circumstances to require the patent owner to license others on reasonable terms as provided for by the terms of Grant No. CA81254 awarded by the National Cancer Institute, U.S. National Institutes of Health.

TECHNICAL FIELD

The subject of the invention is a new vector for oral immunization by using a papillomavirus pseudovirus. This pseudovirus can be used as a vaccine to treat and prevent mucosal infections by pathogens or mucosal tumors. Additionally it can be used in gene therapy.

TECHNICAL BACKGROUND

It is well known that pathogens and immune deficiency are the major causes of various diseases. The human body is frequently invaded by pathogens and damaged by tumors. Therefore, immunity is necessary in protecting the human body from various infections and damages. Many vaccines currently used induce specific immune responses through subcutaneous and intramuscular injections and help the body survive the disease. However, the injections can only induce systemic immune responses but not mucosal immune responses. The injected vaccine fails to treat and prevent those pathogens transmitted through mucosa. Actually many diseases are transmitted through mucosa, for example, HIV.

SUMMARY OF THE INVENTION

The objective of this invention is to make a papillomavirus pseudovirus that is similar to a papillomavirus, but without the capacity of causing disease, and to insert genes or DNA vaccines into papillomavirus-like particles (VLPs) so that it can be used for oral delivery of these gene's to mucosal and systemic lymphoid tissues to induce immune responses for disease prevention and treatment.

The pseudovirus described above is made by disrupting human papilloma virus (HPV)-VLP or bovine papilloma virus (BPV)-VLP, mixing them with plasmids, and reassembling the VLPs with the plasmids inside the VLPs to form the pseudovirus. Thus, the pseudovirus has viral VLPs but may not have any papillomavirus DNA. After the DNA vaccine has been packaged into VLPs, the vaccine can be delivered orally to the mucosal and systemic immune systems. The vaccine in the present application does not contain DNA of the papilloma virus. The DNA vaccine will induce only systemic immune responses by subcutaneous or intramuscular injections. In other words, the pseudovirus in the invention is the papillomavirus VLPs that contain the DNA vaccine. It is prepared by the following steps:

1. HPV-VLPs or BPV-VLPs are mixed with a disruption buffer in 1:1 ratio by vol., and incubated 60 minutes at room temperature; the disruption buffer: ethylene glycol bis(2-aminoethylether) tetraacetic acid (EGTA) 20 mM, dithiothreitol (DTT) 40 mM, sodium chloride (NaCl) 300 mM, Tris-hydrochloric acid (Tris-HCl)(pH 8.0) 100 mM;

2. Plasmids are added in 1/10 of vol, 0.5-1.0 microgram/microliter;

3. A stop buffer is added progressively. The stop buffer; calcium chloride ($CaCl_2$) 25 mM, dimethyl sulfoxide (DMSO) 20% (total stop buffer in vol.); and 4. The mixture is incubated at 4 centigrade for 4 to 12 hours.

This pseudovirus does not cause any disease, and thus can be used for gene therapy. The gene of interest can be inserted into a plasmid that is then packaged into VLPs. Oral administration of the pseudovirus will deliver the gene to intestinal mucosal and systemic lymphoid tissues as well as mucosal epithelium. More importantly, an antigen can be inserted into a plasmid which is packaged into the VLPs to form pseudoviruses, which serve as an oral vaccine to induce protective immune responses. This is different from other vaccines because most other vaccines can only be injected subcutaneously or intramuscularly, but can not be given orally. Other vaccines can induce only systemic immune responses, but not mucosal immune responses. Because many pathogens are transmitted through mucosa, only this pseudovirus can induce effective immune responses to prevent and to treat mucosal infections caused by pathogens. These pathogens include bacteria such as salmonella and viruses such as HIV. Similarly, this pseudovirus can be used to induce immune responses to treat tumors, in particular, mucosal tumors such as colon cancer. This pseudovirus also induces much stronger immune responses than DNA vaccines.

DETAILED DESCRIPTION OF PARTICULAR EMBODIMENT

Example 1

Figure 1:
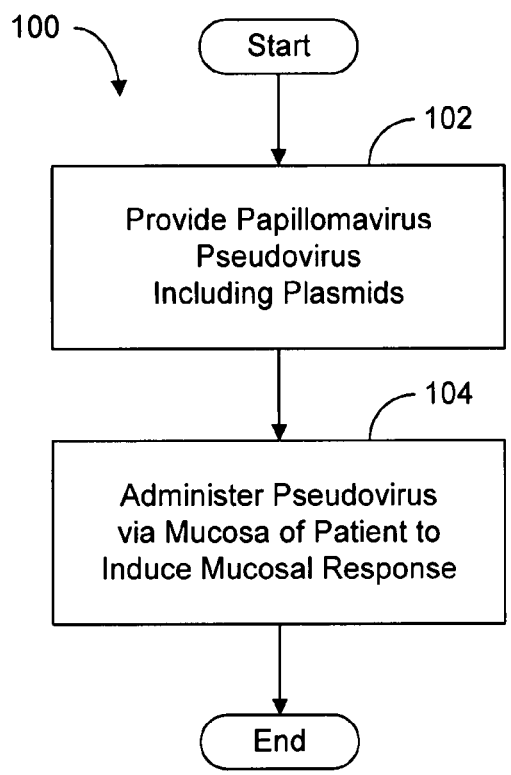
FIG. 1 is a flowchart summarizing a method of treating a patient with a papillomavirus pseudovirus according to the present invention.

First, HPV-VLPs were mixed with disruption buffer at 1:1 proportion by vol., and then incubated at room temperature for 60 min. The disruption buffer was composed of ethylene glycol bis(2-aminoethylether) tetraacetic acid (EGTA) 20 mM, dithiothreitol (DTT) 40 mM, sodium chloride (NaCl) 300 mM, and Tris- hydrochloric acid (Tris-HCl) (pH 8.0) 100 mM. Then, the plasmids (pCI-GLP-LCMV) were added into the mixture in 0.5 microgram/microliter by ratio of 1/10 in vol. Next, stop buffer was progressively added, and the mixture was incubated at 4 centigrade overnight. The stop buffer was composed of calcium chloride ($CaCl_2$) 25 mM, and dimethyl sulfoxide (DMSO) 20% (in vol.). The pseudovirus was subcutaneously injected into C57BL6 mice. Meanwhile, the unpackaged plasmids were injected directly into mice as a control. It was found that the pseudovirus induced more CTLs than the unpackaged plasmids did by using Cr51 release assay or gamma interferon Elispot. The conclusion is that the pseudovirus is more effective than DNA vaccines in inducing cellular immune response.

Example 2

First, BPV-VLPs were mixed with disruption buffer at 1:1 proportion by vol., and then incubated at room temperature for 60 min. The disruption buffer was composed of EGTA 20 mM, DTT 40 mM, NaCl 300 mM, and Tris-hydrochloric acid (Tris-HCl) (pH 8.0) 100 mM. Then, plasmids expressing GLP (Green lantern protein) were added into the mixture in 0.5 microgram/microliter by ratio of 1/10 in vol. Next, the same volume of stop buffer was gradually added, and the mixture was incubated at 4 centigrade overnight. The stop buffer was composed of $CaCl_2$ 25 mM, and DMSO 20% (in vol.). The pseudoviruses were orally administered into mice, and the expression of GLP was examined. GLP was found in intestinal mucosa, mesenteric lymph nodes, and spleen. It is thus demonstrated that the pseudovirus can carry genes to intestinal mucosa and the entire immune system. Therefore, it can be used in gene therapy. When mice were orally administered with unpackaged plasmids encoding GLP, GLP was not found in these tissues.

Example 3

By the same method as described in example 1, a pseudovirus expressing HPV16E7 (HPV and BPV pseudoviruses) was prepared and given to mice orally. The pseudovirus induced specific mucosal and systemic CTLs to the E7 antigen. However, oral immunization with unpackaged plasmid encoding the E7 could not induce any immune response. Therefore, the pseudovirus can be used to induce mucosal and systemic immune responses.

Example 4

By the same method as described in examples 1 and 2, pseudoviruses expressing HPV16E7 (HPV and BPV pseudoviruses) were made by using HPV and BPV VLPs respectively. Mice were orally administered with HPV pseudovirus encoding E7 and then challenged with BPV pseudovirus encoding E7. It was found that HPV pseudovirus prevented mice from the challenge with BPV pseudovirus. Therefore, HPV pseudovirus can provide protective immunity.

Example 5

By the same method as described in examples 1 and 2, the pseudovirus expressing human interleukin 2 (IL-2) was made. Via oral administration, the pseudovirus expressing IL-2 entered intestinal mucosal and systemic lymphoid tissues. It was found that it enhanced the efficacy of generation of mucosal immunity.

FIG. 1 is a flowchart summarizing a method 100 for treating a patient with a papilloma-virus pseudovirus according to the present invention. In a first step 102, a papillomavirus pseudovirus including papillomavirus-VLPs with plasmids contained inside is provided. Then, in a second step 104, the pseudovirus is administered to a patient, via the patient's mucosa, to induce a mucosal response.

Figure 2:
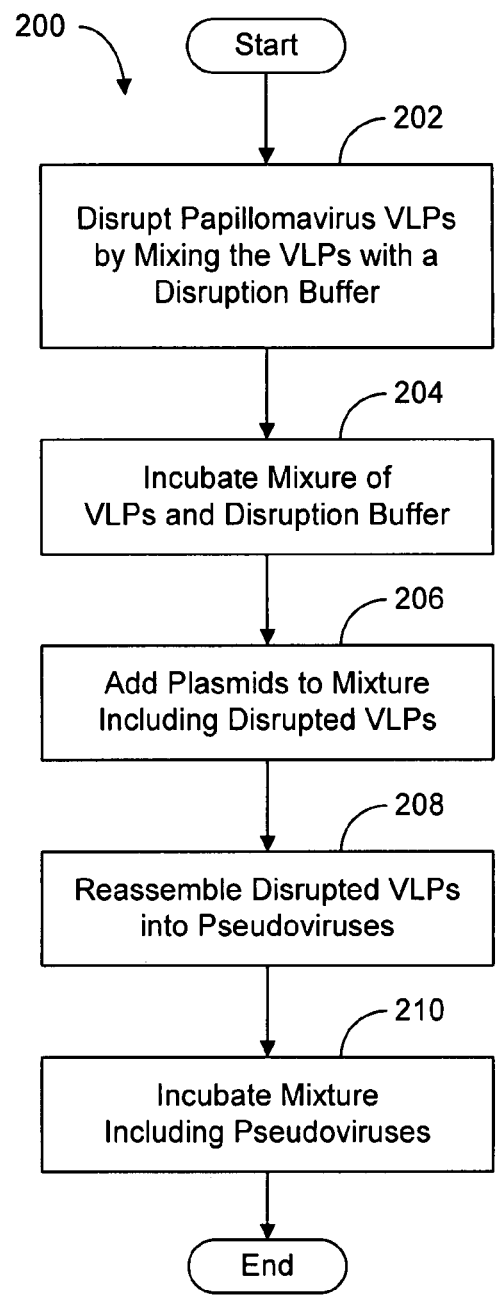
FIG. 2 is a flowchart summarizing a method for making a papillomavirus pseudovirus according to the present invention.

FIG. 2 is a flowchart summarizing a method 200 for making a papillomavirus pseudovirus according to an embodiment of the present invention. In a first step 202, papillomavirus VLPs are disrupted by mixing the VLPs with a disruption buffer. Then, in a second step 204, the mixture of the VLPs and the disruption buffer is incubated. Next, in a third step 206, plasmids are added to the mixture including the disrupted VLPs. In a fourth step 208, the disrupted VLPs are reassembled into pseudoviruses by adding a stop buffer to the mixture such that the plasmids are contained inside the VLPs. Finally, in a fifth step 210, the mixture containing the pseudoviruses is incubated.

We claim:

1. A method for treating a patient with a papillomavirus pseudovirus including plasmids, said method comprising:
   providing said papillomavirus pseudovirus including papillomavirus-VLPs with said plasmids inside; and
   directing that said papillomavirus pseudovirus be administered via the mucosa of said patient to induce a response in a mucosal epithelium of said patient; and
   wherein
   said step of providing said papillomavirus pseudovirus includes making said papillomavirus pseudovirus, said making including disrupting said papillomavirus-VLPs by mixing said papillomavirus-VLPs with a disruption buffer including a chelating agent and reassembling said papillomavirus-VLPs and said plasmids into pseudoviruses of VLPs with said plasmids inside by adding a stop buffer.

2. A method according to claim 1, wherein said plasmids include a gene of a pathogen.

3. A method according to claim 1, wherein said plasmids include therapeutic genes.

4. A method according to claim 3, wherein said pseudovirus is administered to said patient to deliver said therapeutic genes to the cells of said patient.

5. A method according to claim 4, wherein said pseudovirus is administered to said patient orally.

6. A method according to claim 5, wherein said therapeutic genes are delivered to the mucosa of said patient.

7. A method according to claim 6, wherein said therapeutic genes are delivered to the systemic immune system of said patient.

8. A method according to claim 4, wherein said therapeutic genes are delivered to the mucosa of said patient.

9. A method according to claim 1, wherein said papillomavirus-VLPs are one of human papillomavirus-VLPs and bovine papillomavirus-VLPs.

10. A method according to claim 1, wherein:
    said papillomavirus-VLPs are one of human papillomavirus-VLPs and bovine papillomavirus-VLPs; and
    said plasmids express HPV16E7.

11. A method according to claim 1, wherein said pseudovirus is administered to said patient orally.

12. A method according to claim 11, wherein said pseudovirus is administered to said patient to induce a mucosal immune response in said patient.

13. A method according to claim 12, wherein said pseudovirus is administered to said patient to further induce a systemic immune response.

14. A method according to claim 1, wherein said pseudovirus is administered to said patient to induce a mucosal immune response in said patient.

15. A method according to claim 14, wherein said pseudovirus is administered to said patient to further induce a systemic immune response.

16. A method according to claim 1, wherein said plasmids express interleukin 2.

17. A method according to claim 1, wherein said papillomavirus-VLPs are mixed with said disruption buffer in a 1:1 ratio by volume.

18. A method according to claim 1, wherein
the total volume of said stop buffer is substantially equal to the combined total volume of said papillomavirus-VLPs, said disruption buffer, and said plasmids.

19. A method according to claim 1, wherein said chelating agent includes EGTA.

20. A method according to claim 1, wherein said pseudovirus is effective to deliver said plasmids to systemic lymphoid tissues of said patient.

* * * * *